(12) United States Patent
Lin et al.

(10) Patent No.: US 9,371,548 B2
(45) Date of Patent: Jun. 21, 2016

(54) METHOD FOR PRODUCING BUTYRIC ACID, BUTANOL AND BUTYRATE ESTER

(75) Inventors: Yun-Huin Lin, Hsinchu (TW); Hom-Ti Lee, Zhubei (TW); Hsiu-Yin Yin, Zhubei (TW); Sz-Chwun John Hwang, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 13/442,345

(22) Filed: Apr. 9, 2012

(65) Prior Publication Data

US 2012/0264181 A1  Oct. 18, 2012

Related U.S. Application Data

(60) Provisional application No. 61/475,454, filed on Apr. 14, 2011.

(51) Int. Cl.
*C12P 7/52* (2006.01)

(52) U.S. Cl.
CPC ............... *C12P 7/52* (2013.01); *C12P 2203/00* (2013.01)

(58) Field of Classification Search
None
See application file for complete search history.

(56) References Cited

U.S. PATENT DOCUMENTS

| | | | |
|---|---|---|---|
| 4,814,273 A | 3/1989 | Brumm et al. | |
| 5,132,217 A | 7/1992 | Gabelman | |
| 5,563,069 A | 10/1996 | Yang | |
| 5,667,996 A | 9/1997 | Minagawa et al. | |
| 7,455,997 B2 | 11/2008 | Hughes | |
| 7,485,290 B2 | 2/2009 | Ushida et al. | |
| 7,833,778 B2 | 11/2010 | Butler, III | |
| 8,420,359 B2 * | 4/2013 | Sonomoto et al. | 435/160 |
| 2007/0258953 A1 | 11/2007 | Duncan et al. | |
| 2008/0248540 A1 * | 10/2008 | Yang | 435/160 |
| 2010/0124773 A1 | 5/2010 | Yang | |
| 2011/0151529 A1 | 6/2011 | Yang | |

FOREIGN PATENT DOCUMENTS

| | | |
|---|---|---|
| CN | 101487029 | 7/2009 |
| EP | 125983 B1 | 11/1984 |
| EP | 0 546 528 | 6/1993 |
| EP | 2194120 A1 | 6/2010 |
| GB | 2459756 A | 11/2009 |
| WO | WO 2009/154624 | 12/2009 |

OTHER PUBLICATIONS

"Notification of Transmittal of the International Search Report and the Written Opinion of the International Searching Authority, or the Declaration", International Application No. PCT/CN2012/073785, International Filing Date: Apr. 11, 2012, Mailing Date: Jul. 5, 2012.
Atsumi, S. et al. Metabolic engineering of *Escherichia coli* for 1-butanol production. Metabolic Engineering 2008, 10:305-311.
Atsumi, S. et al. Non-fermentative pathways for synthesis of branched-chain higher alcohols as biofuels. Nature 2008, 451(3), 86-90.
Lui, X. et al. Butyric acid and hydrogen production by *Clostridium tyrobutyricum* ATCC 25755 and mutants. Enzyme and Microbial Technology 2006, 38:521-528.
Oshiro, M. et al. Efficient conversion of lactic acid to butanol with pH-stat continuous lactic acid and glucose feeding method by *Clostridium saccharoperbutylacetonicum*. Appl. Michrobiol. Biotechnol. 2010, 87:1177-1185.
Steen, E.J. et al. Metabolic engineering of *Saccharomyces cerevisiae* for the production of n-butanol. Microbial Cell Factories. 2008,7(36), 36-43.
Vissers, M.M.M. et al. Concentrations of Butyric Acid Bacteria Spores in Silage and Relationships with Aerobic Deterioration. J. Dairy Science 2007, 90:928-936.
Wu, Z. et al. Extractive Fermentation for Butyric Acid Production from Glucose by *Clostridium tyrobutyricum*. Biotechnology and Bioengineering 2003, 82:93-102.
Zhu, Y. et al. Adaptation of *Clostridium tyrobutyricum* for Enhanced Tolerance to Butyric Acid in a Fibrous-Bed Bioreactor. Biotechnol. Prog. 2003, 19:365-372.
Mevissen-Verhage et al., "Bifidobacterium, Bacteroides, and Clostridium spp. in fecal samples from breast-fed and bottle-fed infants with and without iron supplement", Journal of Clinical Microbiology, 25(2):285-289 (1987).

* cited by examiner

*Primary Examiner* — Nashaat Nashed
(74) *Attorney, Agent, or Firm* — Finnegan, Henderson, Farabow, Garrett & Dunner LLP

(57) ABSTRACT

The present disclosure is directed to methods for producing butyric acid comprising fermenting a feedstock using a bacterium. The feedstock comprises lactic acid, or the feedstock comprises lactic acid and at least one carbohydrate.

19 Claims, 13 Drawing Sheets

--- : Theoretical maximum butyric acid produced from glucose

FIG. 5

*C. butyricum*

[Graph 1: Glucose + Lactate, y-axis 0-20, showing Lactic acid, Acetic acid, Propionic acid, Butyric acid, Glucose, and OD over time]

[Graph 2: Glucose, y-axis 0-30, showing Lactic acid, Acetic acid, Propionic acid, Butyric acid, Glucose, and OD over time]

X-axis: Time (h)

--- : Theoretical maximum butyric acid produced from glucose

--- : Theoretical maximum butyric acid produced from glucose

METHOD FOR PRODUCING BUTYRIC ACID, BUTANOL AND BUTYRATE ESTER

This application claims priority to U.S. Provisional Application No. 61/475,454, filed on Apr. 14, 2011, which is incorporated herein by reference in its in entirety.

Novel methods for producing butyric acid, butanol and butyrate ester are disclosed herein. The method uses lactic acid or, alternatively, lactic acid and at least one carbohydrate as a feedstock for fermentation to produce butyric acid and butanol with a higher carbon yield than conventional fermentation methods using only carbohydrates as a carbon source.

Acetone-butanol-ethanol fermentation (ABE fermentation) is an anaerobic process that uses bacterial fermentation to produce acetone, butanol and ethanol from carbohydrate. The process also usually uses a strain of bacteria from the *Clostridia* Class. *Clostridium acetobutylicum* is the most well known strain, and *Clostridium beijerinckii* has also been used. In the ABE fermentation process, butyric acid and acetic acid are produced, and the culture then undergoes a metabolic shift and solvents, such as butanol, acetone and ethanol, are formed. The process produces these solvents in a ratio of 3-6-1, or 3 parts acetone, 6 parts butanol and 1 part ethanol. The actual mechanism of the fermentation can be complicated and difficult to control. As a result, the butanol yield is low, and the production of such is further limited by severe product inhibition. It was once a widely used industrial fermentation process. However, since the 1950's, industrial ABE fermentation has been gradually replaced by petroleum chemical methods because the drawbacks made it less profitable compared to the production of these solvents from petroleum.

The fermentation processes are generally limited by low product yield, low productivity, and low product concentration. The low product yield is due to the low conversion rate of substrate to product as a result of the production of $CO_2$ during the fermentation process. The volatile organic compounds that are manufactured during fermentation process include ethanol or butanol. Additionally, large amounts of carbon dioxide are produced, generally 40-50%, and therefore these solvents are called "half-burn fuel."

With the fluctuations of oil prices, the production of biofuels from renewable resources has drawn increasing attention. Various methods to improve the fermentation process have been sought by researchers to convert carbohydrates into butyric acid or butanol with better yield. The yields, however, were not significantly improved.

For example, U.S. Pat. No. 7,455,997 describes a two-step fermentation process using plant-derived feedstock including two polysaccharides, a first one which is more readily hydrolysable and a second one which is more difficult to hydrolyze. The two polysaccharides are hydrolyzed by an acid and by an enzyme sequentially during the process to generate a mixture of fermentation products including, e.g., ethanol, glycerol, acetone, n-butanol, butanediol, isopropanol, butyric acid, methane, citric acid, fumaric acid, lactic acid, propionic acid, etc. U.S. Pat. No. 5,132,217 teaches using nutrients selected from fructose, glucose, glycerol and sucrose as the main carbon source for fermentation in the presence of *Clostridium* to produce butyric acid. The carbon yield is 34% from glucose and 33% from sucrose according to the examples. Another process is described in US 2008/0248540, which provides a yield of up to 48% (g/g), the theoretical conversion rate from glucose to butyric acid. The same publication also discloses a two-step process to convert glucose to butanol.

Improving the Carbon Yield

When using the conventional glucose fermentation process and seeking improvements, a factor to the viability of biofuel production is the generation of $CO_2$. At least one third of the carbon can be lost during the process as a result of the generation of $CO_2$. The present disclosure provides methods for producing butyric acid and butanol with improved carbon conversion and carbon yield compared to conventional carbohydrate fermentation.

SUMMARY

Novel methods are disclosed for producing butyric acid by fermenting a feedstock using a butyric acid-producing bacterium, wherein the feedstock comprises lactic acid or, alternatively, lactic acid and at least one carbohydrate.

The present disclosure is directed to methods of producing butyric acid, comprising fermenting a feedstock with at least one butyric acid-producing bacterium to produce butyric acid, wherein the feedstock comprises lactic acid or, alternatively, lactic acid and at least one carbohydrate. For example, the at least one butyric acid-producing bacterium comprises at least one strain of *Clostridium*.

In some embodiments, the at least one strain of *Clostridium* is chosen from *C. tyrobutyricum*, *C. butyricum* and *C. beijerinckii*. In another embodiment, the at least one strain of *Clostridium* is *C. tyrobutyricum*.

In some embodiments, the at least one carbohydrate is chosen from monosaccharides, disaccharides, polysaccharides, and mixtures thereof. In some embodiments, the at least one carbohydrate is chosen from monosaccharides and disaccharides. For example, the monosaccharide is glucose, xylose, galactose or a mixture thereof. Further for example, the disaccharide is lactose, sucrose, cellobiose, or a mixture thereof. In some other embodiments, the polysaccharide is chosen from starch, glycogen, cellulose, and a mixture thereof. In some embodiments, the at least one carbohydrate comprises at least one soluble carbohydrate obtained from treating biomass with an enzymatic saccharification process.

When the feedstock comprises lactic acid and at least one carbohydrate, in some embodiments of the method of the present disclosure, the weight ratio of lactic acid and the at least one carbohydrate in the feedstock ranges from about 0.1 to about 10, from about 0.3 to about 3, or from about 0.5 to about 1.5.

In some embodiments, the at least one strain of *Clostridium* is *C. tyrobutyricum*, and the feedstock comprises lactic acid and glucose.

In some embodiments of the present disclosure, the fermentation method provides a butyric carbon yield higher than that of a conventional fermentation using carbohydrate(s) as the only substrate. For example, the method provides a butyric carbon yield higher than about 66%, such as a butyric carbon yield higher than 69%.

The methods of the present disclosure generate less $CO_2$ compared to a conventional fermentation using carbohydrates(s) as the only substrate. In some other embodiments, the lactic acid in the feedstock is converted to butyric acid without generation of $CO_2$. For example, the conversion to butyric acid results in no detectable level of $CO_2$.

As provided in some embodiments of the present disclosure, the fermenting step continues for a time chosen from when a substantial amount of the feedstock is consumed, and when no substantial increase in butyric acid is observed. For example, the fermenting step continues for about 15 to about 80 hours, such as for about 30 to about 75 hours.

The addition of lactic acid or, alternatively, lactic acid and at least one carbohydrate may be sequential to the feedstock in any order, before or after the fermenting step commences.

The fermentation method further comprises hydrogenating the butyric acid to produce butanol by chemical or biochemical processes. For example, the hydrogenating step can be conducted using chemical hydrogenation, such as catalytic hydrogenation or transfer hydrogenation. In some other embodiments, the hydrogenating step uses at least one butanol-producing microorganism. For example, the microorganism of the at least one butanol-producing microorganism is a solventogenesis phase of a *Clostridium* strain, such as *C. acetobutylicum, C. beijerinckii, C. aurantibutyricum*, and *C. tetanomorphum*. The fermentation method further comprises esterifying the butyric acid in the presence of a catalyst and an alcohol to produce a butyrate ester. In some other embodiments, the butyrate ester may be further reduced to obtain butanol.

Additional features of the disclosure will be set forth in part in the description which follows, and in part will be obvious from the description, or may be learned by practice of the disclosed method. The features of the disclosure will be realized and attained by means of the elements and combinations particularly pointed out in the appended claims.

Particular aspects of the disclosure are described in greater details below. The terminologies and definitions as used in the present application as clarified herein are intended to represent the meaning of the Applicants in their disclosure. The patent and scientific literature referred to herein are hereby incorporated by reference in their entireties. The terms and definitions provided herein control, if in conflicts with terms and/or definitions incorporated by reference.

It is to be understood that both the foregoing general description and the following detailed description are exemplary and explanatory only and are not restrictive of the claimed invention.

The accompanying drawings, which are incorporated in and constitute a part of this specification, illustrate several embodiments of the disclosure and together with the description, serve to explain the principles of the disclosure.

BRIEF DESCRIPTION OF THE DRAWINGS

FIG. 5 graphically illustrates the time course of free cell, substrate, and product concentrations in fermentations by *C. butyricum* using glucose and L-lactic acid as substrates (top), and using glucose as the sole substrate (bottom).

Figure 1:
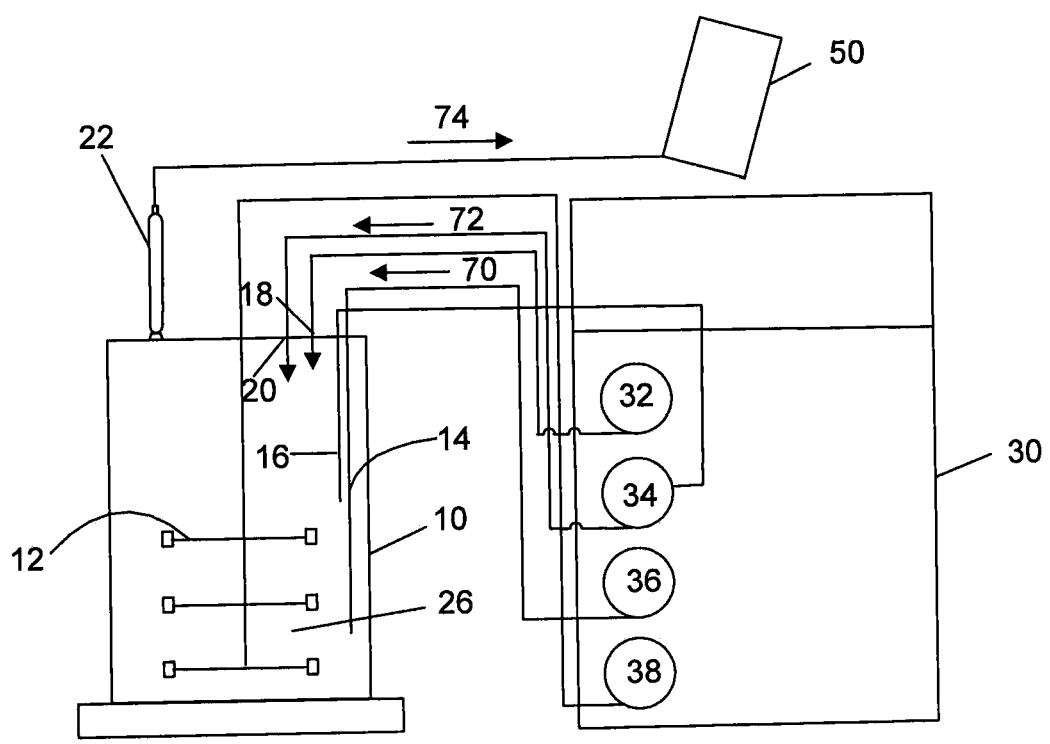
FIG. 1 illustrates a free suspension system used for fermentation.

FIG. 8 graphically illustrates the time course of free cell, substrate, and product concentrations in a fermentation by *C. tyrobutyricum* using glucose and L-lactic acid as substrates.

FIG. 9 graphically illustrates the time course of free cell, substrate, and product concentrations in a fermentation by *C. tyrobutyricum* using L-lactic acid as the sole substrate.

FIG. 10 graphically illustrates the time course of free cell, substrate, and product concentrations (top graphs) and the volume of $CO_2$ (bottom graphs) generated in fermentations by *C. tyrobutyricum* and *C. butyricum* in a stirred-tank reactor system.

FIG. 11 graphically illustrates the time course of free cell, substrate, and product concentrations (top graphs) generated in a repeated batch fermentation by *C. tyrobutyricum* in a stirred-tank reactor system. The substrate for the first batch includes glucose and L-lactic acid. The substrate for the second batch includes glucose, L-lactic acid and acetic acid. The substrate for the third batch contains only L-lactic acid.

FIG. 12 graphically illustrates the time course of free cell, substrate, and product concentrations in a fermentation using *C. tyrobutyricum* with glucose and L-lactic acid as substrates in a stirred-tank reactor system.

FIG. 13 graphically illustrates the time course of free cell, substrate, and product concentrations in a fermentation by *C. tyrobutyricum* using xylose and L-lactic acid as substrates in an immobilized pack-bed system.

DESCRIPTION

Definitions

As used herein, the term "acid," such as in lactic acid and butyric acid, is intended to encompass free acid and salts which are generated by combination of such acids and suitable bases which may be present in the medium during the process, for example, lactic acid may include: free lactic acid, sodium lactate, ammonium lactate, lithium lactate, calcium lactate, potassium lactate, magnesium lactate, ammonium lactate, and aluminum lactate. In addition, the terms "butyric acid" and "butyrate" are interchangeable to describe the acid or its deprotonated form, depending on the pH value of its environment. The same applies to other acids, for example, lactic acid/lactate, propionic acid/propionate, and acetic acid/acetate.

Unless otherwise specified, chemical names described herein refer to all isomeric forms of the chemical names, such as enantiomers, diastereomers, and conformational isomers. For example, the term "lactic acid," "glucose," "xylose," "galactose" refers to both D and L isomers. When the carbohydrate is capable of existing in both open-chain and cyclic form, both conformations and both alpha and beta isomers of the chair form are encompassed.

The singular forms "a," "an," and "the" include plural reference unless the context indicates otherwise. Any term ending with "(s)" encompasses the term in both singular and plural form.

The terms "approximately" and "about" mean to be nearly the same as a referenced number or value. As used herein, the terms "approximately" and "about" should be generally understood to encompass ±10% of a specified amount, frequency or value. Further, all numbers expressing the quantities used in the specification and claims, for example, concentration, reaction conditions, time, temperature and yield, are modified by the term "about," unless otherwise indicated. As used herein, when a numerical range is given, both ends of the range are included.

The term "substantial" or "substantially" mean of real worth or importance, or considerable value. For example, a substantial increase or decrease means a change greater than 5% of the previous measured value.

As used herein, the terms "fermenting" and "fermentation" refer to a process in which microorganisms such as bacteria, yeast, and other small organisms metabolize one or more substances to produce the energy and chemicals needed to live and re-produce. This process of chemical reactions will produce some forms of by-product. Microorganisms are capable of generating a wide array of molecules as end points to fermentation. For example, carbon dioxide and ethanol are the by-products produced in brewing by yeast and pyruvate is converted into lactic acid in lactic acid fermentation. Fermentation is an ATP-generating process in which organic compounds act as both donors and acceptors of electrons, and it can take place in the absence of oxygen. Berg, M. Jeremy et al. Biochemistry chap. 16 (2002). As used herein, a "conventional fermentation" refers to a fermentation using only carbohydrate(s) as substrate(s).

As used herein, the term "feedstock," or "fermentation medium," is the raw material for fermentation. It may be a medium suitable for fermentation. It may further comprise fermentable substrates. The substrates may include, but not limited to, carbohydrates and/or lactic acid, or mixtures thereof. Other substances may also be present in the medium as needed. For example, NaOH, $NH_4OH$, $NaH_2PO_3$, $Na_2HPO_3$, citric acid, HCl, $NH_4Cl$, may be added to adjust the pH value of the feedstock to a desired value, for example, pH 6, or to adjust other physical, chemical or physiological properties.

As used herein, the term "microorganism" refers to a living organism too small to be seen with the naked eye, including bacteria, fungi, protozoans, algae, and viruses.

As used herein, a strain of a bacterium may be a wild-type strain or a mutant strain. Inoculum size (w/v) refers to a ratio of the weight of cells (for example, immobilized cell beads) relative to the total volume of feedstock.

Evaluating Carbon Retention Efficiency

As used herein, the term "carbon yield" refers to the number of carbons retained in the desired product(s) relative to the number of carbon in the substrate(s) in a chemical or biological transformation:

$$\text{Carbon Yield} = \frac{\text{Number of carbons in desired product(s)}}{\text{Number of carbons in substrate(s)}}$$

To evaluate the efficiency of carbon retention in the desired products, "carbon yield" is compared among fermentations using different feedstock and bacteria. For example, in a fermentation using glucose as the substrate to generate butyric acid or butanol, the possible chemical transformations are:

Glucose($C_6H_{12}O_6$)→1 Butylic acid($C_4H_8O_2$)+2$CO_2$+ 2$H_2$

Glucose($C_6H_{12}O_6$)→1 Butanol($C_4H_{10}O$)+2$CO_2$+$H_2O$

One molecule of glucose ($C_6H_{12}O_6$, 6 carbons) is transformed in a conventional fermentation process to generate one butyric acid ($C_4H_8O_2$, 4 carbons) or one butanol ($C_4H_{10}O$, 4 carbons), therefore the butyric carbon yield is 4/6=0.66. The measured carbon yield, however, is often lower than the theoretical yield.

When butyric acid is the predominant product in the fermentation, "butyric carbon yield" may be used as an indication of carbon retention efficiency. For example, in a fermentation using glucose and lactic acid as substrates, the efficiency of butyric acid generation can be expressed as follows:

Butyric carbon yield =

$$\frac{\text{Number of carbon in butyric acid}}{\text{Number of carbons in feedback (glucose + lactic acid)}}$$

The gaseous product $CO_2$ is usually not a desired product in fermentation, and is usually considered "carbon loss." However, acetic acid and propionic acid are common products in fermentation and may be considered desired products in the "total carbon yield." For a fermentation which generates a significant amount of acetic acid and/or propionic acid, it is more appropriate to consider the "total carbon yield" to evaluate carbon retention efficiency. For example, the total carbon yield for a fermentation using glucose and lactic acid as substrates is expressed as follows:

$$\text{Total carbon yield} = \frac{\substack{\text{Number of carbons in desired product} \\ \text{(butyric acid + propionic acid + acetic acid)}}}{\substack{\text{Number of carbons in feedstock} \\ \text{(lactic acid + carbohydrarte(s))}}}$$

Improving Carbon Yield

The disclosure herein provides a novel method for producing butyric acid and butanol with improved carbon conversion and carbon yield, especially butyric carbon yield.

In some embodiments of the present disclosure, this is achieved by using lactic acid or, alternatively, lactic acid and at least one carbohydrate as substrates for the fermentation process. By using this combination as feedstock in the fermentation, a higher carbon yield, especially butyric carbon yield, can be achieved, compared to the conventional fermentation using only carbohydrate(s) as substrate(s). For example, butyric carbon yield in the presently disclosed method may exceed about 66% (or 0.49 g/g), the theoretical butyric carbon yield in conventional fermentation, assuming the carbohydrate(s) proceed in the conventional fermentation mechanism. Without being bound by a particular theory, it may be that the lactic acid fermentation proceeds through a different biochemical pathway, which does not involve the generation of $CO_2$, that may explain why the total carbon yield of the methods disclosed herein exceeds the theoretical carbon yield of a traditional ABE pathway.

A comparative fermentation using lactose as the sole substrate with *C. tyrobutyricum* was studied. This fermentation may involve another different biosynthetic pathway. Although quantitative carbon yield may be achieved after 48 hours, acetic acid and propionic acid are generated in significant amount (about 50%), compared with other fermentations. Consequently the butyric carbon yield is relatively low (about 50%).

Fermentation of Lactic Acid or Alternatively Combination of Lactic Acid and at Least One Carbohydrate The present disclosure is directed to methods of producing butyric acid, comprising fermenting a feedstock with at least one butyric acid-producing bacterium to produce butyric acid, wherein the feedstock comprises lactic acid or, alternatively, lactic acid and at least one carbohydrate.

The disclosed method can increase the carbon yield of butyric acid by fermenting feedstock comprising lactic acid or, alternatively, lactic acid and at least one carbohydrate. Assuming butyric acid is the only fermentation product, the chemical equation of such conversion is as follows:

1 lactic acid($C_3H_6O_3$)+3$H^+$+3$e^-$→0.75 butyric acid ($C_4H_8O_2$)+1.5 $H_2O$ The theoretical conversion rate is 0.73 g/g and carbon yield is 100%.

Further, the method produces butyric acid by fermenting a feedstock containing lactic acid or, alternatively, lactic acid and at least one carbohydrate with at least one butyric acid-producing bacterium, for example, a *Clostridium* strain. Examples of *Clostridium* strain include, but are not limited to *C. tyrobutyricum, C. thermobutyricum, C. butyricum, C. populeti, C. cadaveros, C. cellobioparum, C. cochlearium, C. pasteurianum, C. roseum, C. rubrum,* and *C. sporogenes*; such as *C. tyrobutyricum, C. butyricum* and *C. beijerinckii.*

Carbohydrates suitable for the disclosed method of producing butyric acid include, but are not limited to, fermentable monosaccharides, disaccharides, polysaccharides, and mixtures thereof. The monosaccharide may be a pentose, or a hexose. Examples of pentose include, but are not limited to, arabinose, lyxose, ribose, xylose, arabinose, ribulose, xylulose, and mixtures thereof; for example, xylose. Examples of hexose, include, but are not limited to, allose, altrose, glucose, mannose, gulose, idose, galactose, talose, psicose, fructose sorbose, tagatose, and mixtures thereof; such as glucose and fructose; for example, glucose. Examples of disaccharide include, but are not limited to, sucrose, lactulose, lactose, maltose, trehalose, cellobiose, and mixtures thereof; such as, lactose, sucrose and cellobiose; for example, lactose. Examples of polysaccharides include, but not limited to, cyclodextrin, starches, glycogen, arabinoxylans, cellulose, guar gum, gum arabic, chitin and pectins. The carbohydrates may be soluble carbohydrates obtained from treating biomass with an enzymatic saccharification process. Suitable sources of biomass feedstock include agricultural residues such as corn stovers, corn cobs, and rice straw, and processing wastes such as corn fiber. Suitable microorganisms for the saccharification include, but are not limited to, bacteria, yeasts, and filamentous fungi.

When the feedstock comprises lactic acid and at least one carbohydrate, the weight ratio of lactic acid to the at least one carbohydrate in the feedstock may range from about 0.1 to about 10, such as from about 0.3 to about 3, or from about 0.5 to about 1.5.

Unless otherwise specified, "the carbon yield(s)" refers to either "butyric carbon yield" or "total carbon yield," as a general indication for carbon retention efficiency regardless whether butyric acid is the major product. The method disclosed herein using lactic acid or, alternatively, lactic acid and at least one carbohydrate as feedstock provides good "butyric carbon yield" and "total carbon yield." The "butyric carbon yield" and the "total carbon yield" may be higher than 45%, higher than 50%, higher than 55%, higher than 60%, higher than 66%, higher than 67%, higher than 68%, higher than 70%, higher than 72%, higher than 73% or higher than 82%. The butyric carbon yield and total carbon yield may range from 45% to 100%, from 50% to 100%, from 55% to 95%, from 60% to 90%, from 63% to 90%, from 66% to 90%, from 67% to 85%, or from 69% to 85%.

The butyric carbon yield and total carbon yield may vary for a number of reasons, for example, family and strains of the bacterium, whether the bacterium is immobilized or free suspension, carbohydrate(s), concentration and ratio of the lactic acid and carbohydrate(s), temperature, stirring speed of the fermentor, mode of fermentation (batch, continuous, etc.). In another embodiment of the present disclosure, under appropriate fermentation conditions, the fermentation process can provide a higher "butyric carbon yield" than a conventional fermentation using only carbohydrate(s) as the substrate(s). Higher "butyric carbon yield" may be achieved by (1) suppressing the generation of acetic acid, propionic acid and other products, and/or (2) decreasing $CO_2$ generation and minimizing carbon loss. The butyric carbon yield may exceed 66%, the theoretical (maximum) butyric carbon yield. For example, the butyric carbon yield may be greater than 66%, greater than 67%, greater than 68%, greater than 70%, greater than 72%, greater than 73%, greater than 75% or greater than 82%, for example, from 66% to 90%, from 67% to 88%, or from 69% to 85%.

For example, the lactic acid in the feedstock can be converted to butyric acid and other products with little or no production of $CO_2$. The efficiency of lactic acid to butyric acid conversion in the disclosed fermentation process can be evaluated as follows:

$$\text{Lactic to butyric acid carbon yield} = \frac{\text{Number of carbons in produced butyric acid}}{\text{Number of carbons in lactic acid}}$$

The butyric acid generated from lactic acid in a fermentation experiment using a combination of lactic acid and carbohydrate(s) as the substrates is calculated by subtracting the theoretical (maximum) butyric acid generated by the carbohydrate(s) from the total butyric acid produced. Assuming that the carbohydrates (e.g., glucose) are converted with theoretical efficiency (about 66% carbon yield), the lactic acid still generates good carbon yield compared to conventional fermentation using only carbohydrate(s) as substrate(s). For example, the lactic acid may generate a good carbon yield of greater than 45%, greater than 55%, greater than 60%, greater than 65%, greater than 70%, greater than 80%, greater than 90%, and 100%.

The presently disclosed fermenting process can generate less $CO_2$ than a conventional fermentation. The lactic acid in the feedstock may be converted to butyric acid with generation less than 1 molar equivalent of $CO_2$, such as less than 0.5 molar equivalent of $CO_2$. In further embodiments, the lactic acid in the feedstock is converted to butyric acid without generation of $CO_2$.

The time period for which the method ferments can depend on a number of factors. For example, the fermentation time may depend on the strain of bacteria, concentration of the substrates, mode of operation, etc. Lactic acid may be consumed more rapidly, more slowly than the carbohydrate(s), or they may be consumed at about equal rate. In many circumstances, the butyric acid and other products are still generating after all the substrates are consumed. The fermentation is allowed to continue until a substantial amount of the substrates is consumed, and/or no substantial increase in butyric acid is observed. For example, the amount of butyric acid usually stops increasing, or even decreases after a certain time due to product inhibition. The duration of the fermentation process may last from about 10 to about 80 hours, for examples, from about 20 to about 80 hours, from about 30 to about 75 hours, from about 35 to about 70 hours, or from about 40 to about 55 hours.

The order of adding substrate(s) and the bacteria into the feedstock may be added in any order and is not restricted. Each substrate may be added multiple times before and during the fermentation commences. Lactic acid and carbohydrate(s) may be added into the feedstock sequentially and in any order. For example, the feedstock containing all substrates may be prepared before the inoculation. One or more substrates may be added into the feedstock after inoculation repeatedly. In some other examples, the feedstock may be separated from the bacteria (e.g., immobilized cell beads) and removed from the fermentor, and fresh feedstock is then added into the remaining bacteria in the fermentor to start a second fermentation. Such operation may be repeated as many times as appropriate.

In some embodiments where the feedstock comprises lactic acid and at least one carbohydrate, the ratio of lactic acid to carbohydrate(s) may vary. For example, the weight ratio of lactic acid to carbohydrate may range from about 0.1 to about 10, such as ranging from about 0.3 to about 3, ranging from about 0.5 to about 1.5. In another example, the ratio may be about 1.

The butyric acid generated from the fermentation process may be further transformed to other organic molecules, such as butanol. For example, butyric acid may be hydrogenated to generate butanol. The hydrogenating step may be a chemical hydrogenation, such as catalytic hydrogenation or transfer hydrogenation, in which the butyric acid is reduced by hydrogen gas or a hydrogen donor in the presence of a metal catalyst. The hydrogenating step may be carried out using a butanol-producing microorganism, for example, a bacterium, or a solventogenesis phase of a bacterium, such as a *Clostridium*. Examples of *Clostridium* strains suitable for such transformation include, but are not limited, to *C. acetobutylicum, C. beijerinckii, C. aurantibutyricum*, and *C. tetanomorphum*. The butyric acid obtained from the fermentation may further undergo esterification to generate butyrate ester, for example, in the presence of a catalyst and an alcohol, such as the methods described in U.S. Patent Application Publication No. 2010/0124773. The butyric acid may be extracted from the fermentation feedstock using an amine solvent. Non-limiting examples of catalyst include lipase, and non-limiting examples of alcohol include methanol, ethanol, propanol and butanol. The catalyst maybe an enzyme, such as a lipase. The esterification may take place without solvent if the alcohol is butanol, or with one or more solvents such as n-hexane, acetone, acetonitrile, cyclohexane, 2-octanol, Alamine 336, and a mixture thereof. The resulting butyrate ester may be further reduced to butanol using chemical or biochemical methods.

Fermentation Apparatus

The fermentation can be carried out in either batch, fed-batch, or continuous mode, either to optimize yield or to lower production cost. A suitable apparatus for the disclosed fermentation process may be a free suspension system, such as the one illustrated in FIG. 1. The system includes a feedstock (26) with a cell suspension placed in a tank fermentor (10), which is equipped with a mechanical stirrer (12), a thermometer (14) and a pH meter (16), all connecting to or controlled by the integrated control station (30). The integrated control station (30) controls the pH value of the fermentation by adding an acid solution (32) and a base solution (34) through tubings (70 and 72) to the acid and base inlets of the fermentor (18 and 20), the fermentation temperature by a thermostat (36), and the stirring speed (38). An optional gas collecting device (50) may be attached to any fermentor described above to collect the gases, such as $CO_2$ and $H_2$, generated during the fermentation through a gas outlet on the top of the fermentor (22) through a tubing (74). The gas generated may be analyzed by gas chromatography.

In yet another embodiment of the present disclosure, the method involves immobilizing the cells in beads of, e.g., polyvinyl alcohol (PVA) first. For example, the cell beads may be added to a bottle filled with a feedstock and the fermentation takes place in the sealed bottle.

Figure 2:
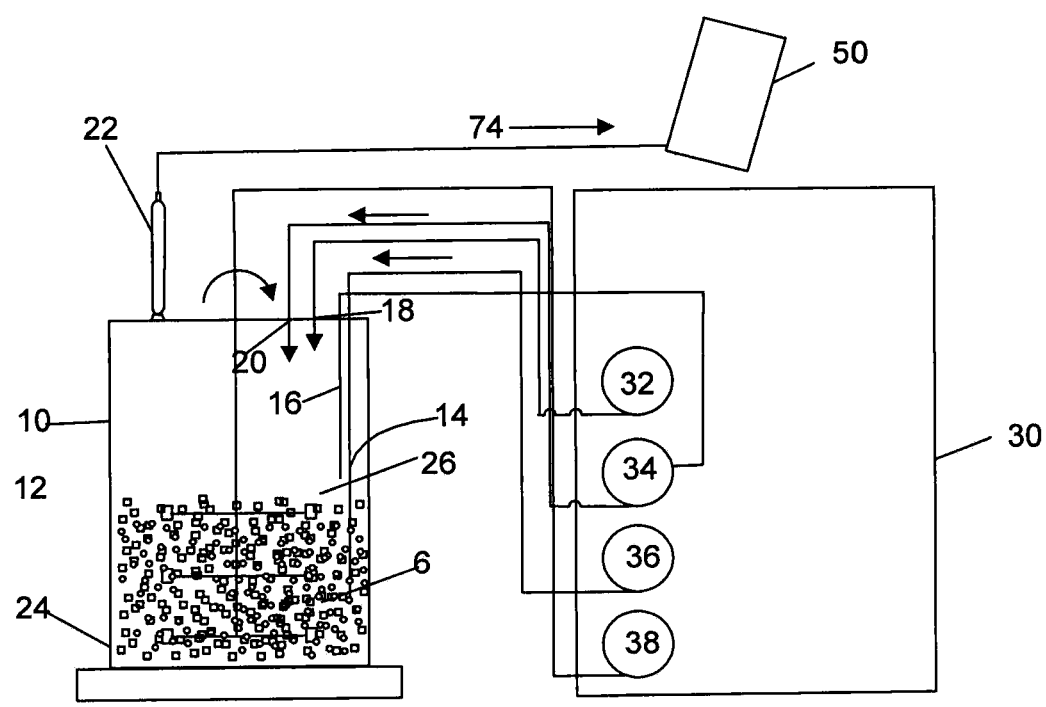
FIG. 2 illustrates a stirred-tank reactor system used for fermentation.

In a further embodiment of the present disclosure, the method uses immobilized cell beads in a stirred-tank reactor system, such as the one illustrated in FIG. 2. The system includes immobilized cell beads (24) with the feedstock (26) that is placed in the fermentor (10), which is equipped with the mechanical stirrer (12), the thermostat (14) and the pH meter (16), all connecting to or controlled by the integrated control station (30). The integrated control station (30) controls the pH value of the fermentation by adding the acid solution (32) and the base solution (34) through the tubings (70 and 72) to the acid and base inlets of the fermentor (18 and 20), the fermentation temperature by the thermostat (36), and the stirring speed (38). The optional gas collecting device (50) may be attached to any fermentor described above to collect the gases, such as $CO_2$ and $H_2$, generated during the fermentation through the gas outlet on the top of the fermentor (22) through the tubing (74). The collected gas may be analyzed by gas chromatography.

Figure 3:
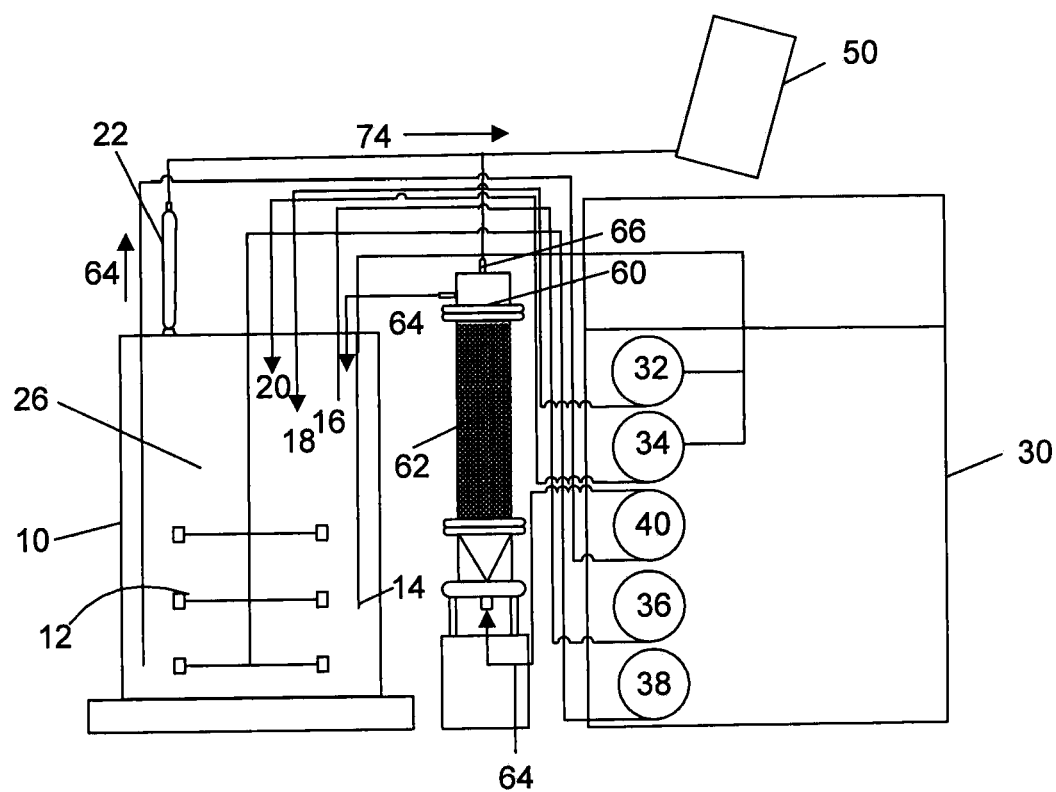
FIG. 3 illustrated an immobilized pack-bed system used for fermentation.
Figure 4:
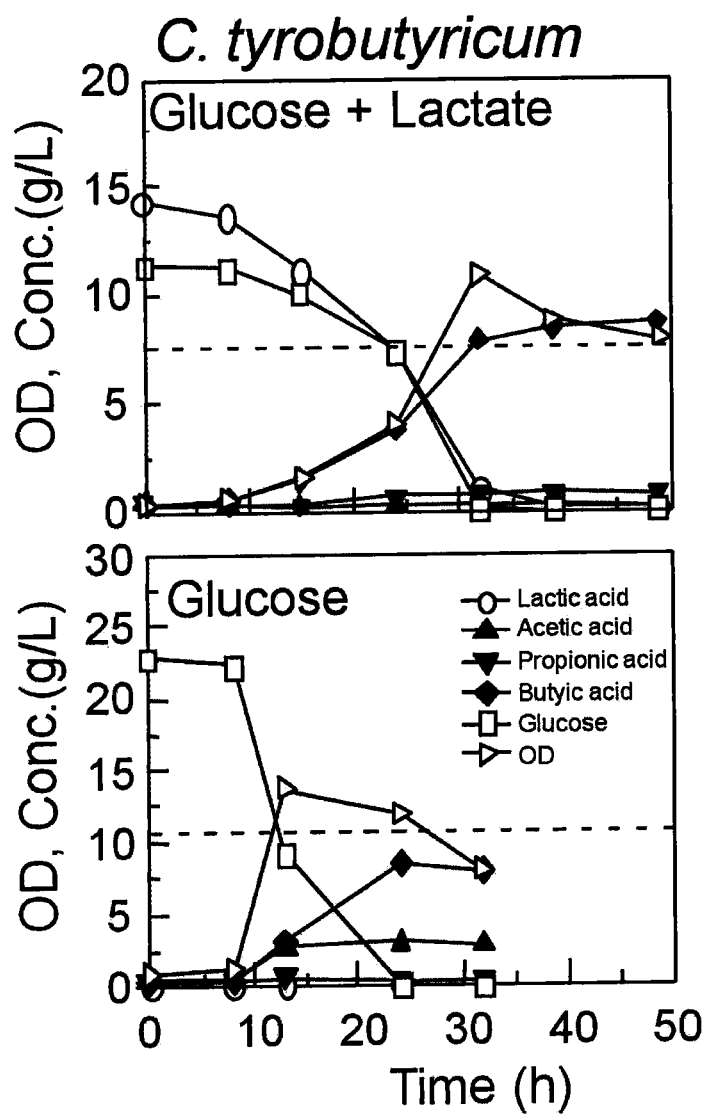
FIG. 4 graphically illustrates the time course of free cell, substrate, and product concentrations in fermentations by *C. tyrobutyricum* using glucose and L-lactic acid as substrates (top), and using glucose as the sole substrate (bottom).
Figure 6:
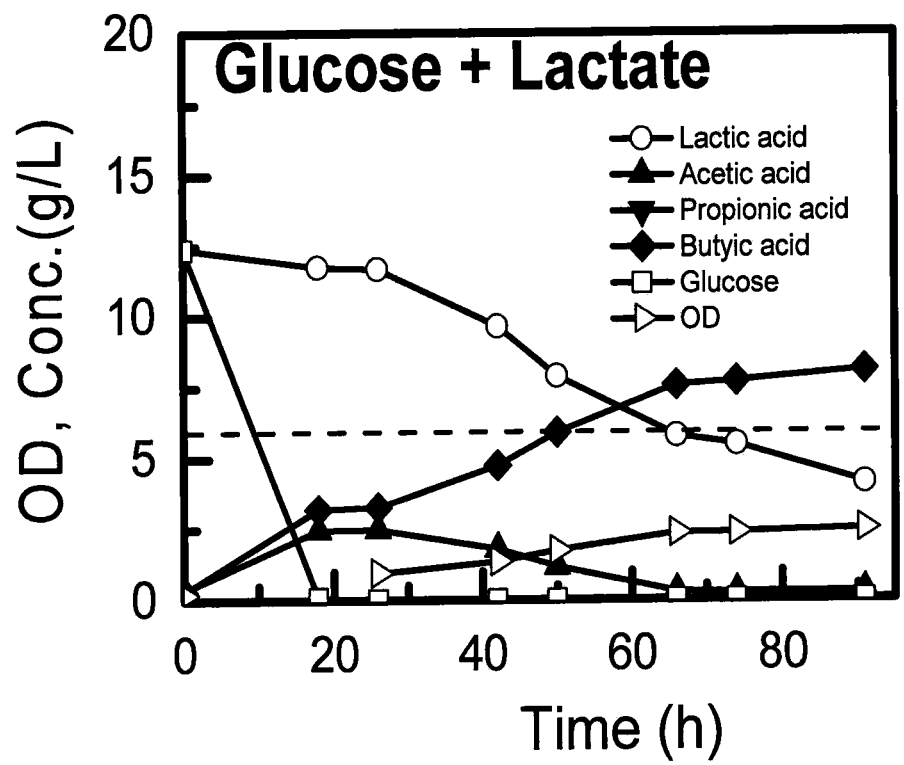
FIG. 6 graphically illustrates the time course of free cell, substrate, and product concentrations in a fermentation by *C. beijerinckii* using glucose and L-lactic acid as substrates.

In addition, the immobilized cell beads may be used in a recirculating pack-bed fermentation system comprising a fermentor and a pack-bed bioreactor, such as the system illustrated in FIG. 3. The system includes the feedstock (26) that is placed in the fermentor (10), which is equipped with the mechanical stirrer (12), the thermostat (14) and the pH meter (16), all connecting to or controlled by the integrated control station (30). The integrated control station (30) controls the pH value of the fermentation by adding the acid solution (32) and the base solution (34) through tubings to the acid and base inlets of the fermentor (18 and 20), the fermentation temperature by the thermostat (36), and the stirring speed (38). The fermentation system also includes a packed-bed bioreactor (60) containing immobilized cell beads (62) which is connected to the stirred-tank fermentor (10) through the recirculation loop (64). The control station (30) also contains a pump (40) to transport the feedstock from the top of the fermentor through the recirculation loop (64) into the bottom of the pack-bed bioreactor. The gas generated from the process is released through the gas outlets on the top of the fermentor and the bioreactor (22 and 66) to the optional gas collecting device (50) through the tubing (74). The collected gas may be analyzed by gas chromatography.

The following examples further illustrate the disclosure. They are merely illustrative of the disclosure and its various beneficial properties of certain embodiments. The following examples should not be construed as limiting the scope of present disclosure.

EXAMPLES

The practice of the present disclosure will employ, unless otherwise indicated, conventional techniques of cell biology, cell culture and fermentation which are within the skill of the art. Such techniques are explained fully in the literature.

Culture and Media

The microorganisms used in the study, *Clostridium* tyrobutyricum (ATCC 25755), *Clostridium butyricum* (IAM 19001), and *Clostridium beijerinckii* (ATCC 8260), were purchased from Bioresource Collection and Research Center (BCRC) and used in this study. The stock culture was kept in serum bottles under anaerobic conditions at 4° C., and was pre-cultured in a serum bottle containing 100 ml of Reinforced Clostridial Medium (RCM, Merck) anaerobically with agitation at 37° C. for 48 hr prior to use.

The basal medium contained the following ingredients in per liter of deionized water: 5 g of yeast extract, 5 g of peptone, 3 g of ammonium sulphate, 1.5 g of $KH_2PO_4$, 0.6 g of $MgSO_4.7H_2O$ and 0.03 g of $FeSO_4.7H_2O$. Wu et al., Biotechnology and Bioengineering 2003, 82(1), 93-102. The feedstock was prepared by adding appropriate substrate(s) to the basal medium. All media and feedstocks were sterilized by autoclaving at 121° C., 15 psig, for 30 min prior to use.

Cell Immobilization

To grow the cells for immobilization, a 5-L fermentor filled with 4-L of the basal medium containing glucose and lactic acid as the substrates was inoculated with about 300 mL of a cell suspension prepared in serum bottles and then allowed to grow for 7 days until the cell concentration reached an optical density ($OD_{600}$) of about 5.

The cells were immobilized in phosphorylated PVA gel beads according to the method described in Chen, K., "Immobilization of microorganism with phosphorylated polyvinyl alcohol (PVA) gel." *Enzyme Microbiob. Technol.* 1994, 16, 679-83. The cells were harvested by centrifugation at 6,500 rpm (KUBOTA, model 7780) for 10 min and suspended in an aqueous solution of PVA, about 9% (w/v), with a ratio of 20 g wet cell per liter of PVA solution. The cell suspension and the PVA solution were thoroughly mixed, and the PVA-cell mixture was dropped into a saturated boric acid and sodium phosphate solution and gently stirred for 1-2 hr to form spherical beads. The resulting beads of 3-4 mm diameter were rinsed with water.

Analysis

Free cell density was analyzed by measuring the optical density of the cell suspension at a wavelength of 600 nm ($OD_{600}$) with a spectrophotometer (OPTIZEN, model 2120UV plus).

Analysis of the liquid products, for example, organic acids and carbohydrates, was performed on HPLC (Agilent HP-1100) equipped with Aminex HPX-87H column (300× 7.8 mm), a column oven at 75° C., and a refractive index detector. The mobile phase was 18 mM $H_2SO_4$ at a flow rate of 6 ml/min. The concentrations of carbohydrates and organic acids were determined according to a standard calibration curve.

Analysis of a gas product, for example, $CO_2$ and $H_2$, was performed on GC (YL6100 GC) equipped with ShinCarbon ST 100/120 mesh column (2 meter×1 mm ID micropacked). The temperatures of the injector and detector were set at 100° C. and 200° C., respectively. The carrier gas was He with a flow rate of 10 ml/min. The carbon dioxide peak was identified by comparison of its retention time with that of a standard.

Example 1

Batch Fermentation in Free Cell Suspension System

Batch fermentations of three *Clostridium* strains, *C. tyrobutyricum*, *C. butyricum*, and *C. beijerinckii* were investigated. The experiments were conducted in free suspension system as illustrated in FIG. 1. The system includes a 2-L tank fermentor, a pH meter connecting to the integrated control station, which controls the pH value of the fermentation by adding acid/base solution to the fermentor.

Each fermentation was performed in 1.0 L feedstock containing glucose and L-lactic acid as the substrates (concentrations shown in Table 1). Anaerobiosis was reached by sparging the medium with $N_2$. The feedstock pH was adjusted to 6.0 with 2 N NaOH before inoculation with 100 mL of cell suspension prepared as described above. Each experiment was carried out at 37° C. and the pH was controlled at about 6±0.1 using 2 N NaOH solution. The fermentation was continued until it ceased to produce detectable butyric acid due to product inhibition. For *C. tyrobutyricum* and *C. butyricum*, a separate fermentation using only glucose as the substrate was carried out to compare the carbon yields and to simulate the conventional glucose fermentation. Each fermentation was continued until no increase of butyric acid concentration is observed, the time period specified in Table 1.

Each batch fermentation process was repeated twice for fermentation kinetics studies. Samples were taken at regular intervals for the analysis of free cell, substrate, and product concentrations. The time course of the concentrations are illustrated in FIGS. 4-6. The butyric carbon yields, the substrate/butyrate ratios, and the time period for each fermentation are summarized below in Table 1. The horizontal dash line indicates the concentration of theoretical maximum butyric acid produced from glucose.

TABLE 1

Comparison of carbon yield from fermentations using different bacteria

| Feedstock | lactic acid/ glucose | lactic acid/ glucose | lactic acid/ glucose |
|---|---|---|---|
| FIG. No. | FIG. 4 | FIG. 5 | FIG. 6 |
| Bacteria | *C. tyrobutyricum* | *C. butyricum* | *C. beijerinckii* |
| Glucose (g/L) | 11.4 | 12.8 | 12.4 |
| L-Lactic acid (g/L) | 14.3 | 15.7 | 12.4 |
| Butyric carbon yield | 56% | 40% | 51% |
| Lactic to butyric acid carbon yield | 48% (49 hr)*[1] | not determined*[2] (41 hr) | 29% (91 hr) |
| Comparative*[3] | | | |
| Glucose (g/L) | 22.9 | 22.1 | — |
| Glucose to butyric acid carbon Yield | 36% (32 hr) | 37% (41 hr) | — |

*[1]Fermentation time shown in parentheses.
*[2]Yield too small to be determined.
*[3]Based on the experiments using glucose as sole substrate.

The carbon yield varies with the *Clostridium* strain used in the fermentation. *C. tyrobutyricum* provides 56% butyric carbon yield overall, while lactic acid itself provides 48% carbon yield (assuming the conversion of glucose to butyric acid is at its theoretical yield, 66%), see FIG. 4. When *C. butyricum* was used, a portion of lactic acid was utilized by the strain, although a large amount of lactic acid remained unchanged throughout the fermentation (see FIG. 5, top). That is, the specific strain does not convert lactic acid as efficiently as *C. tyrobutyricum* does, but the consumption of lactic acid is still achievable. The observation is consistent with the result of the fermentation using glucose as the sole substrate (see FIG. 5, bottom), which provides comparable carbon yields (40% with lactic acid v. 37% without lactic acid). Finally, the fermentation using *C. beijerinckii* consumed glucose within the first 20 hours of the fermentation, but the bacterium converted lactic acid at a much slower rate. After 80 hours of fermentation, there was about ⅔ of the lactic acid consumed by the strain and about ⅓ of the unreacted lactic acid remaining in the feedstock. (FIG. 6). In this example, *C. tyrobutyricum* converts both glucose and lactic acid with almost equal efficiency, both being completely consumed after 30 hours. The reaction provides 56% butyric carbon yield overall, while lactic acid itself provides 48% carbon yield, assuming the conversion of glucose to butyric acid is at its theoretical yield (66%).

Example 2

Immobilized Cell Beads in a Sealed Bottle

In Example 2, the study investigated the effects of the lactic acid-carbohydrate combination on carbon yields in fermentation by immobilized *C. tyrobutyricum* beads in sealed bottles. In the study, the feedstock was prepared using a modified basal medium, in which a phosphate buffer solution (consisting of 0.2M $Na_2HPO_4$ and 0.2M $NaH_2PO_4$) replaces distilled water. The feedstock for the first experiment contained only 3.3 g/L glucose as the substrate. The feedstock for the second experiment included 3.3 g/L glucose and 5.9 g/L L-lactic acid as the substrates, and the feedstock for the third experiment included only 5.7 g/L L-lactic acid as the substrate.

For each experiment, 100 mL of the feedstock was placed in a 168-mL serum bottle, and a phosphate buffer solution of 0.2M $Na_2HPO_4$ and 0.2M $NaH_2PO_4$ was used to maintain the medium pH throughout the experiment. Anaerobiosis was reached by sparging the medium with $N_2$. The pH of the feedstock was adjusted to about 6.0 before inoculation with 5 g of PVA-immobilized *C. tyrobutyricum* beads.

Each experiment was carried out at 37° C. and agitated at 150 rpm. The fermentation was continued until no increase of butyric acid concentration was detected. Each batch fermentation process was repeated twice for fermentation kinetics studies. Samples were taken at regular intervals for the analysis of free cell, substrate, and product concentrations. The time course of the concentrations are illustrated in FIGS. 7-10. The starting concentration of the substrates and the carbon yields are summarized below in Table 2. The horizontal dash line indicates the concentration of theoretical maximum butyric acid produced from glucose.

TABLE 2

Comparison of carbon yield from fermentations using different substrates

Figure 7:
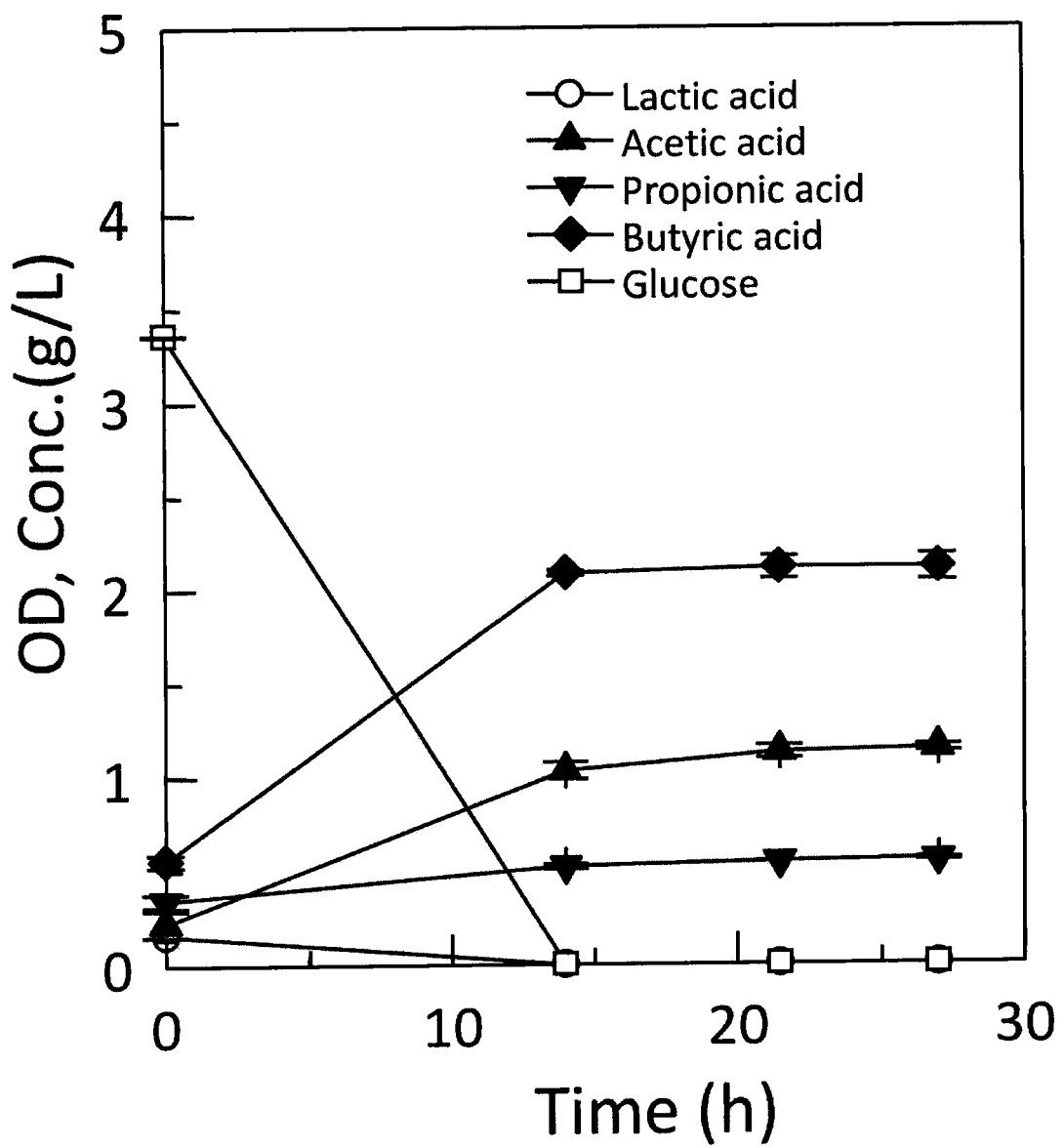
FIG. 7 graphically illustrates the time course of free cell, substrate, and product concentrations in a fermentation by *C. tyrobutyricum* using glucose as the sole substrate.
Figure 8:
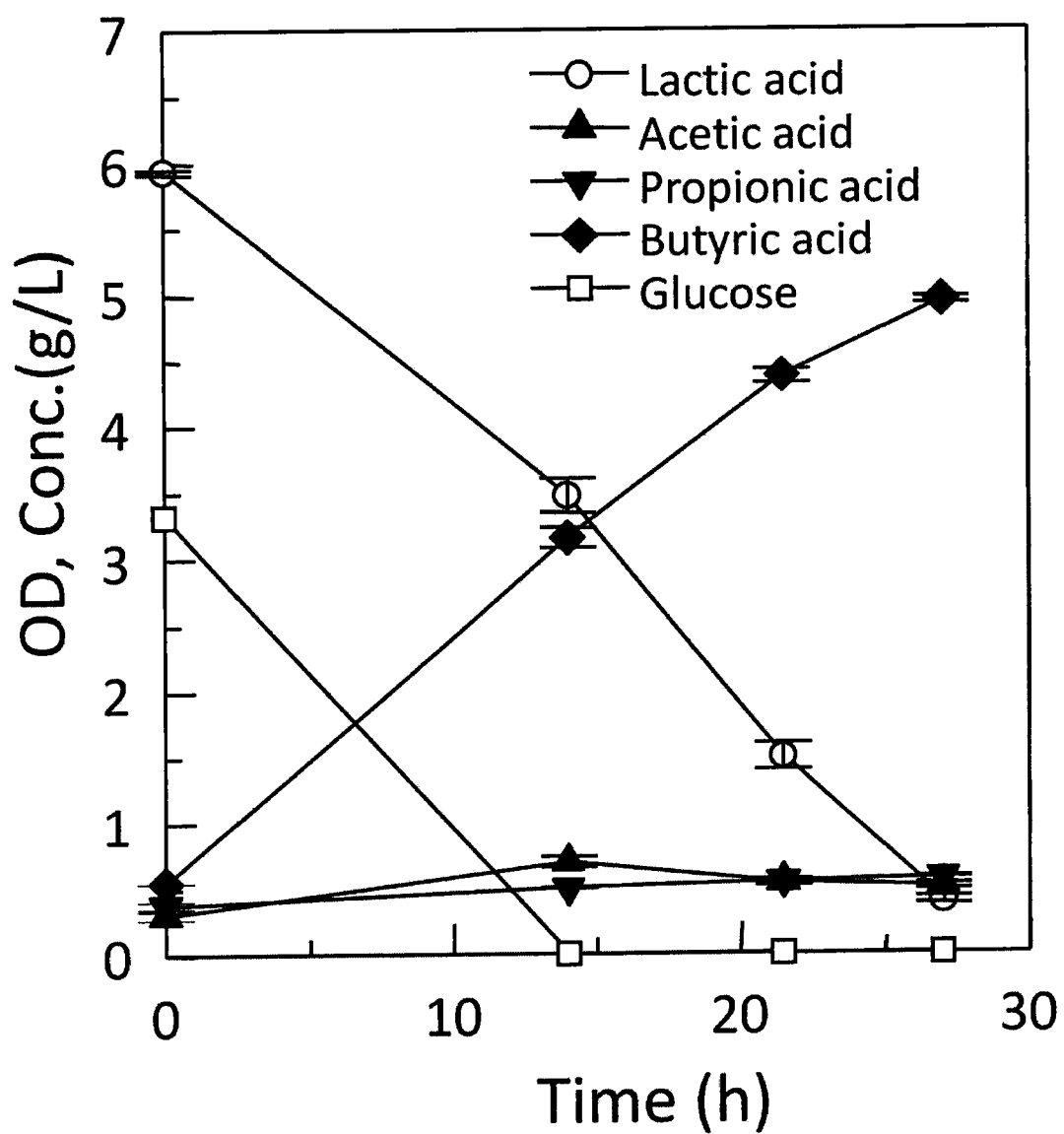
Figure 9:
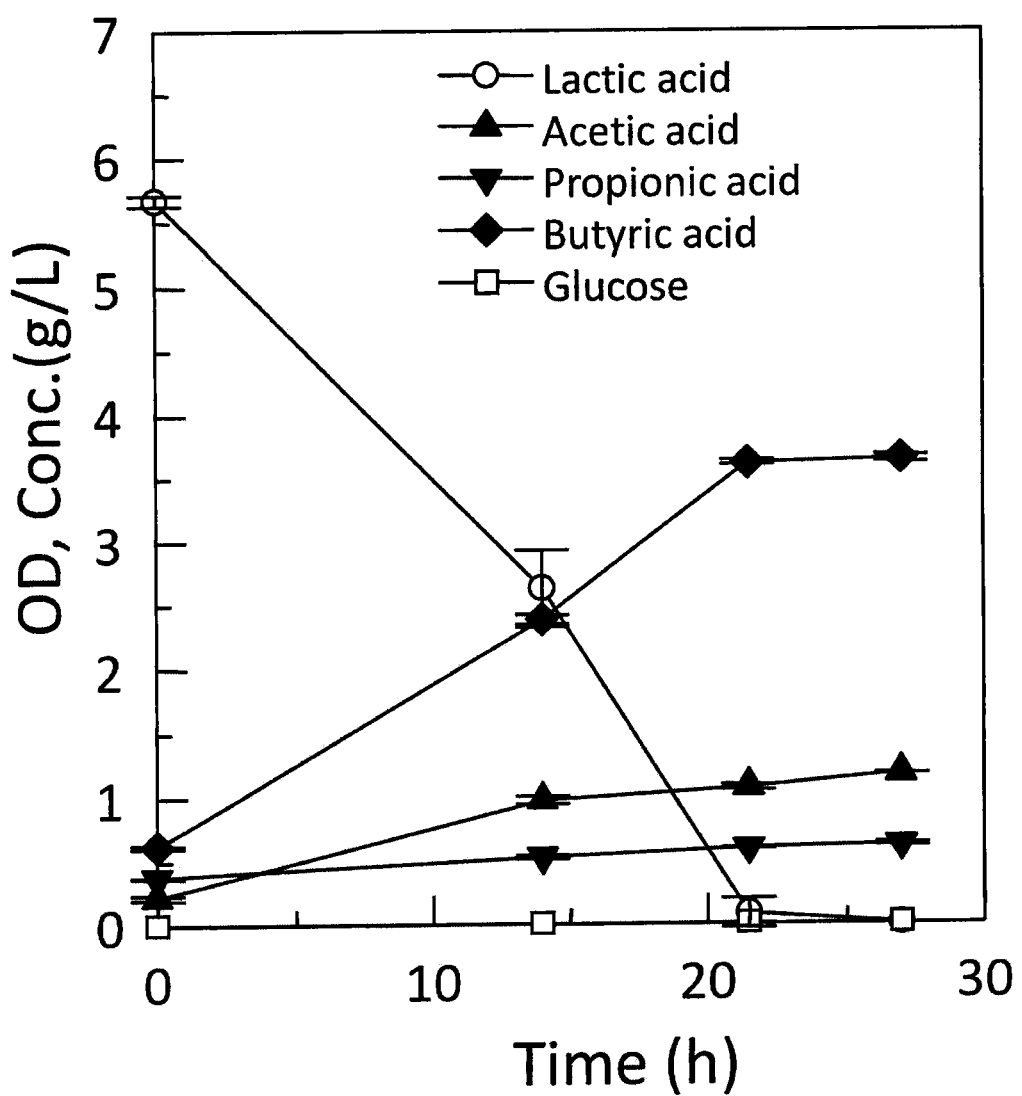

| Feedstock | glucose only | lactic acid/ glucose | lactic acid only |
|---|---|---|---|
| FIG. No. | FIG. 7 | FIG. 8 | FIG. 9 |
| Glucose (g/L) | 3.3 | 3.3 | — |
| L-Lactic acid (g/L) | — | 5.9 | 5.7 |
| Lactose (g/L) | — | — | — |
| Butyric carbon yield | 61% | 69% | 73% |
| Total carbon yield | 93% | 74% | 96% |
| Fermentation time | 27 hr | 27 hr | 27 hr |

When glucose is used as the sole substrate, as in the first experiment, the difference between total carbon yield and butyric carbon yield is greater than when a combination of glucose and L-lactic acid is used, because higher amounts of acetic acid and propionic acid are generated during the fermentation. See FIG. 7. In addition, the butyric carbon yield (61%) is much higher than that of free cell fermentation (see Table 1, 36%), because the immobilized cell beads can be used repeatedly for a long period of time, which may cause cell adaptation to endure higher butyrate concentration, thereby resulting in a higher butyric carbon yield. The second experiment using a feedstock containing both glucose and L-lactic acid affords 69% butyric carbon yield (higher than the theoretical yield), while suppressing the generation of acetic acid and propionic acid (the difference between total carbon yield and butyric carbon yield is only 5%). See FIG. 8. Third, when L-lactic acid is used as the sole substrate, butyric acid is produced in an significant amount, although acetic acid and propionic acid are also generated (the difference between total carbon yield and butyric carbon yield is 23%). See FIG. 9. The total carbon yield, 96%, is very close to the theoretical value (100%). In view of the above, the combination of lactic acid and carbohydrate as substrates in fermentation exceeds those results anticipated under conventional fermentation using glucose as the only substrate, and in some instances may be deemed synergistic with the improvement of the butyric carbon yield.

Example 3

Batch Fermentation-Immobilized Stirred-Tank Reactor

In Example 3, the experiments studied the effects of bacteria on carbon yields of fermentation using an immobilized stirred-tank reactor system, illustrated in FIG. 2. The apparatus included a 2-L stirred tank fermentor equipped with a mechanical stirrer, a pH meter connected to an integrated control station, which controls the pH value of the fermentation by adding acid or base solution to the fermentation tank. The fermentation commenced when the immobilized cell beads are added to the fermentation tank. The gas generated during fermentation is collected through an outlet on the top of the fermentor and can be analyzed by gas chromatography.

For each bacterium of *C. tyrobutyricum* and *C. butyricum*, the batch fermentation was performed in a stirred tank fermentor. After the fermentor was filled with the feedstock, containing glucose and L-lactic acid as substrates (concentrations shown in Table 3), anaerobiosis was reached by sparging the medium with $N_2$. The pH of the medium was adjusted to 6.0 with 2 N NaOH before inoculation with 70 g of PVA-immobilized cell beads containing either *C. tyrobutyricum* or *C. butyricum*. The fermentation was carried out at 37° C., agitated at 600 rpm, and the pH was maintained at about 6±0.1. The reaction was allowed to continue until butyric acid ceased to generate due to product inhibition.

Figure 10:
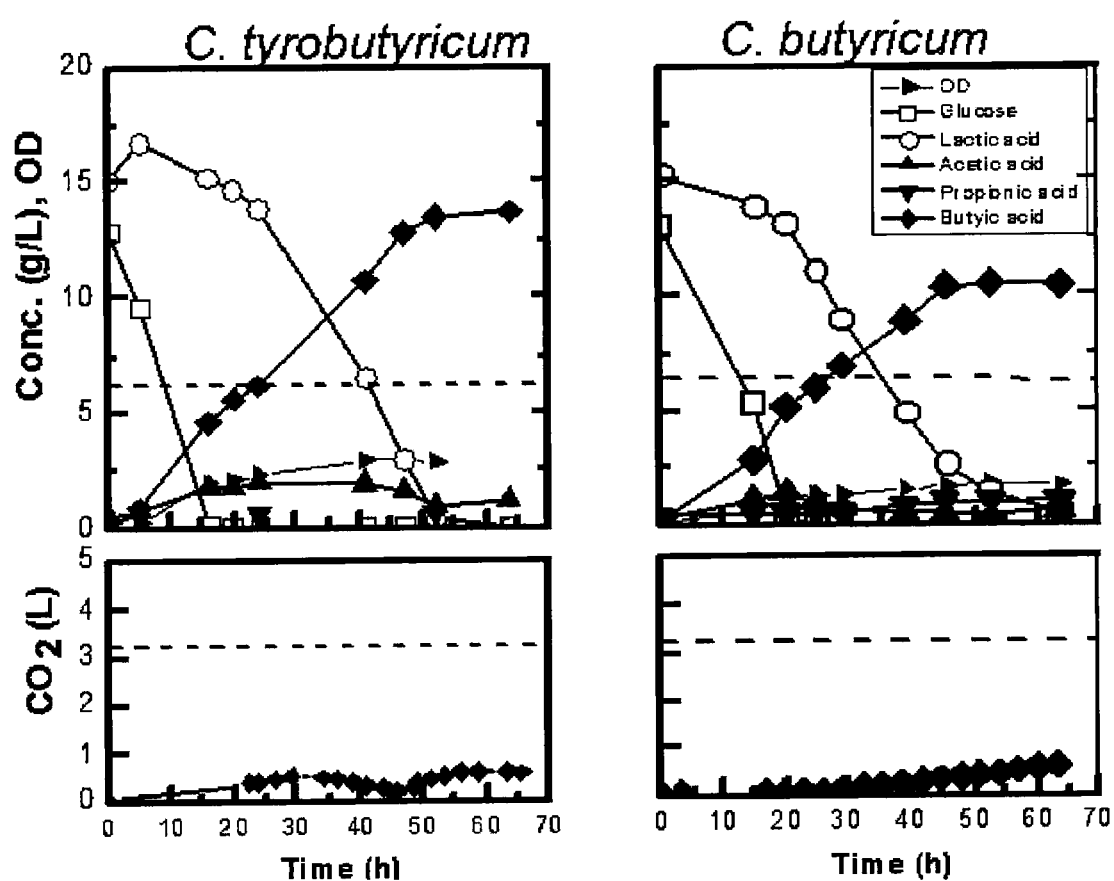

The batch fermentation process was repeated twice for fermentation kinetics studies. Samples were taken at regular intervals for the analysis of free cell, substrate, and product concentrations, and the gas generated from fermentation (e.g., $H_2$, and $CO_2$) was collected and analyzed by GC. The time course of the concentrations and the volume of $CO_2$, are illustrated in FIG. 10. The starting concentration of the substrates and the carbon yields are summarized below in Table 3. The horizontal dash line indicates the concentration of theoretical maximum butyric acid produced from glucose.

TABLE 3

Carbon yield from fermentations in immobilized stirred-tank reactor using different bacteria

| | Bacterium | |
|---|---|---|
| | *C. tyrobutyricum* | *C. butyricum* |
| Glucose (g/L) | 12.8 | 13.0 |
| L-Lactic acid (g/L) | 15.1 | 15.2 |
| Butyric carbon yield | 67% | 51% |
| Total carbon yield | 69% | 52% |
| Fermentation time | 64 hr | 64 hr |

Theoretical $CO_2$ produced from glucose in a conventional fermentation process (without lactic acid) with 12.9 g glucose is:

$$= \frac{12.9 \text{ g}}{180 \text{ g/mol}} \times 2(\text{mol/mol}) \times 22.4(\text{L/mol}) = 3.2 \text{ L}$$

The $CO_2$ generated during the fermentation was monitored. As illustrated in the bottom graphs of FIG. 10, the accumulated amount of $CO_2$ observed was less than 1.0 L (less than 0.5 molar equivalent) throughout the process, far less than the theoretical amount expected in a conventional fermentation using glucose alone. This suggests a different biosynthetic pathway which reduces the $CO_2$ production during the fermentation.

Example 4

Repeated Batch Fermentation

In Example 4, the experiments studied repeated batch fermentation by re-using the same immobilized cell beads in a stirred tank reactor system, which is described in Example 3 and illustrated in FIG. 2.

Figure 11:
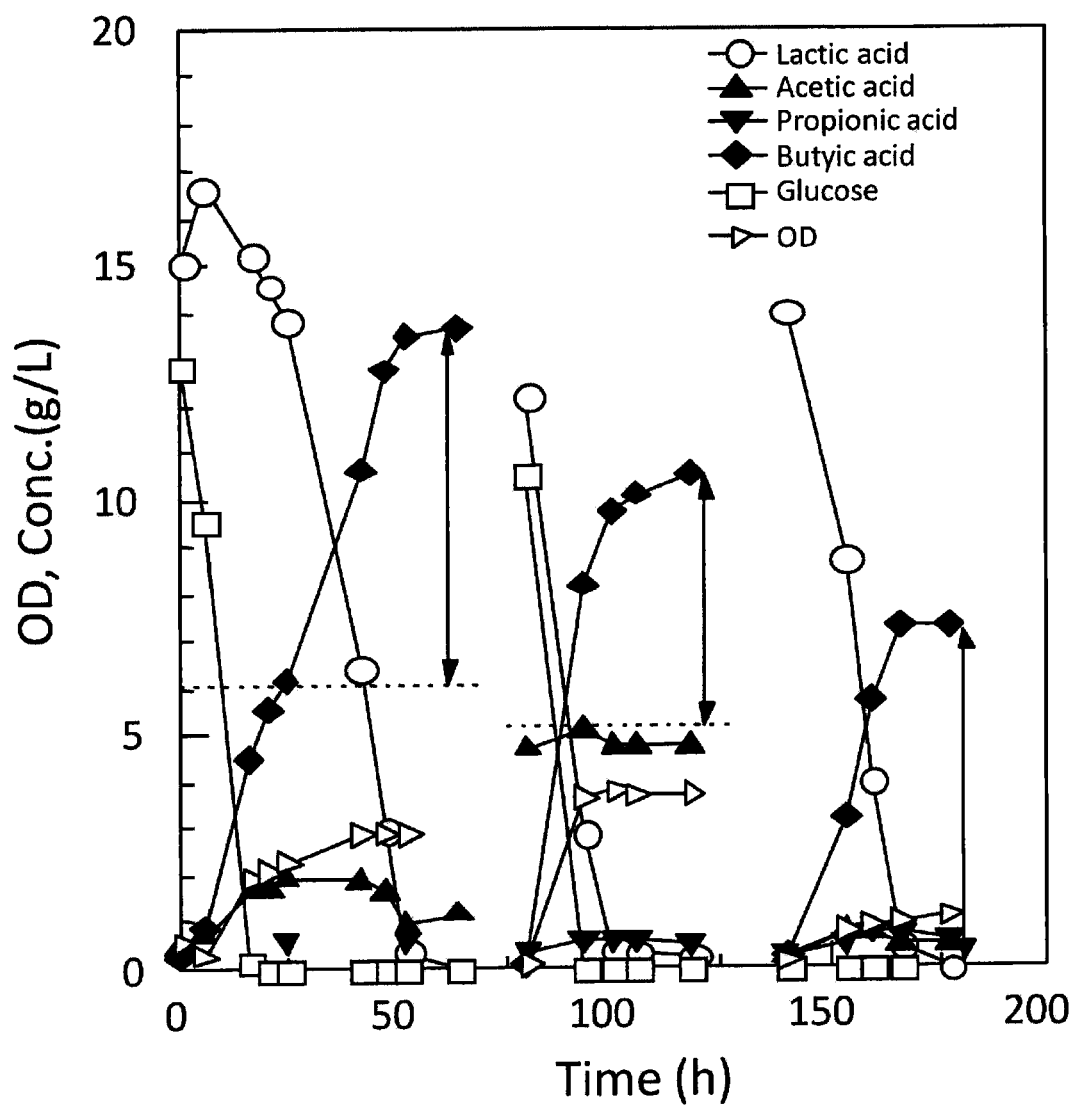

The batch fermentation of *C. tyrobutyricum was performed in a* 2-L stirred tank fermentor, and 1.0 L feedstock containing glucose (13 g/L) and L-lactic acid (15 g/L) was used in the first fermentation cycle. Anaerobiosis was reached by sparging the medium with $N_2$. The pH of the medium was adjusted to 6.0 with 2 N NaOH before inoculation with 70 g of immobilized *C. tyrobutyricum* beads (inoculum size about 5% w/v). The experiment was carried out at 37° C., agitated at 600 rpm and the pH was maintained at around 6±0.1. Samples were taken at regular intervals for the analysis of free cell, substrate, and product concentrations. The time course of the concentrations is illustrated in FIG. 11. The starting concentration of the substrates and the carbon yields are summarized below in Table 4. The fermentation was continued until no more butyric acid was generated (about 70 hours after fermentation commenced). The feedstock was removed, and the cell beads remained in the fermentor. A butyric carbon yield of 65% was achieved and the butyric carbon yield for lactic acid was 64% assuming the glucose was converted with theoretical yield of 66%. The horizontal dash line indicates the concentration of theoretical maximum butyric acid produced from glucose.

TABLE 4

Carbon yield from repeated batch fermentation

|  | First batch | Second batch | Third batch |
| --- | --- | --- | --- |
| glucose (g/L) | 12.8 | 10.5 | — |
| L-lactic acid (g/L) | 15.1 | 12.2 | 14.0 |
| acetic acid (g/L) | — | 4.7 | — |
| butyric carbon yield | 65% | 63% | — |
| lactic to butyric acid carbon yield | 64% | 60% | 68% |
| fermentation time | 64 hr | 38 hr | 37 hr |

In the second batch, fresh feedstock with additional acetic acid was added to the fermentor at the 80th hour, butyric acid was generated during the course of the reaction, even though the concentration of acetic acid was artificially high. The possible product inhibition by artificially adding acetic acid did not seem to suppress the production of butyric acid, and the butyric carbon yields of both substrates and of lactic acid were only slightly lower than those of the first batch (63% and 60% vs. 65% and 64%). The fermentation was stopped after 40 hours, and the feedstock was removed. In the third batch, a fresh feedstock containing only L-lactic acid was fermented with the same immobilized cell beads. The lactic acid was converted to butyric acid with 68% carbon yield. The study demonstrates that reproducible carbon yields by recycling the immobilized cell beads in repeated batch fermentation can be achieved, even under a high concentration of acetic acid. It also demonstrates that each substrate may be sequentially added into the feedstock in the presence of the bacterium.

Example 5 in Example 5, the experiment provided a fermentation process using immobilized *C. tyrobutyricum* beads. The procedure and the fermentation system were substantially similar to those described in Example 3.

Figure 12:
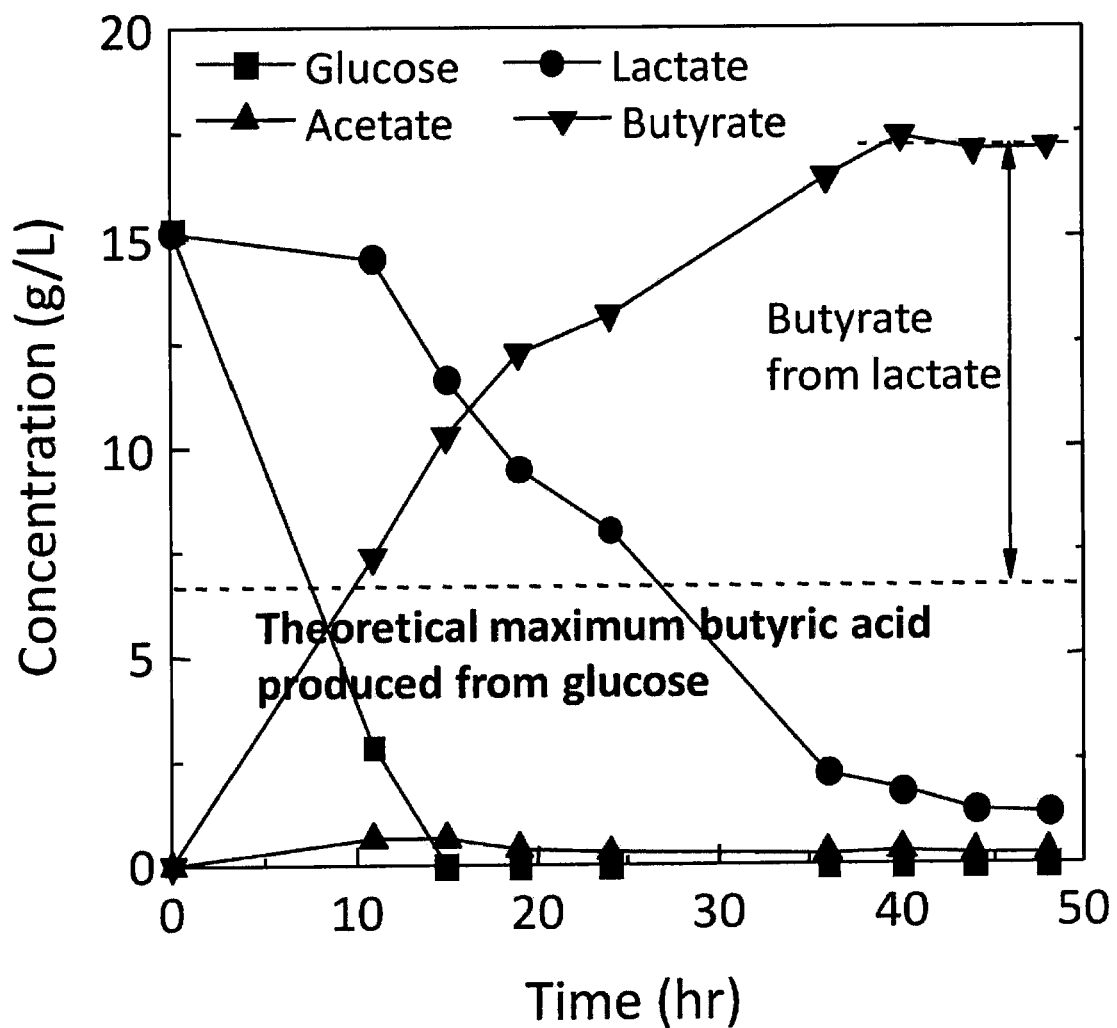

The batch fermentation was performed in a 2-L stirred tank fermentor. After the fermentor was filled with the feedstock containing glucose (15 g/L) and L-lactic acid (15 g/L), anaerobiosis was reached by sparging the medium with $N_2$. The pH of the medium was adjusted to 6.0 with 2 N NaOH before inoculation with 70 g of PVA-immobilized cell beads containing *C. tyrobutyricum* (inoculum sizes about 5% w/v). The fermentation was carried out at 37° C., agitated at 600 rpm, and the pH was maintained at 6±0.1 by adding 2N NaOH solution. The reaction was allowed to continue until butyric acid ceased to be generated due to product inhibition. The time course of the concentrations is illustrated in FIG. 12, in which the horizontal dash line indicates the concentration of the theoretical maximum butyric acid produced from glucose. The final butyric acid concentration was 17.2 g/L, and the amount of acetic acid in the product was very low. The butyric carbon yield was 83%, far exceeding the theoretical yield of 66% from a conventional fermentation. Assuming glucose was converted with the theoretical carbon yield, the conversion from lactic acid to butyric acid was quantitative. That is, no carbon loss occurred through the generation of $CO_2$. The exceedingly high carbon yield in this example suggests an alternative biosynthetic pathway of butyric acid from lactic acid, which reduces the generation of $CO_2$ and increases the maximum carbon yield, compared to the fermentation without adding lactic acid.

Example 6

Combination of Lactic Acid and Xylose in Packed-Bed Fermentation System

In Example 6, the study investigated the applicability of the fermentation process using carbohydrates other than glucose. A packed-bed fermentation system used in the following experiments is illustrated in FIG. 3. The fermentation system included a 0.5-L packed-bed bioreactor connected to a 2-L stirred-tank fermentor through a recirculation loop powered by a pump in the integrated control station. The integrated control station adjusts the pH value and temperature inside the fermentor. A pump in the control station transports the feedstock from the top valve of the fermentor through the recirculation loop into the bottom of the pack-bed bioreactor. The air generated from the process is released through the top of the bioreactor and fermentor to a gas collecting device. The fermentation was operated under well-mixed conditions with controlled pH and temperature.

Figure 13:
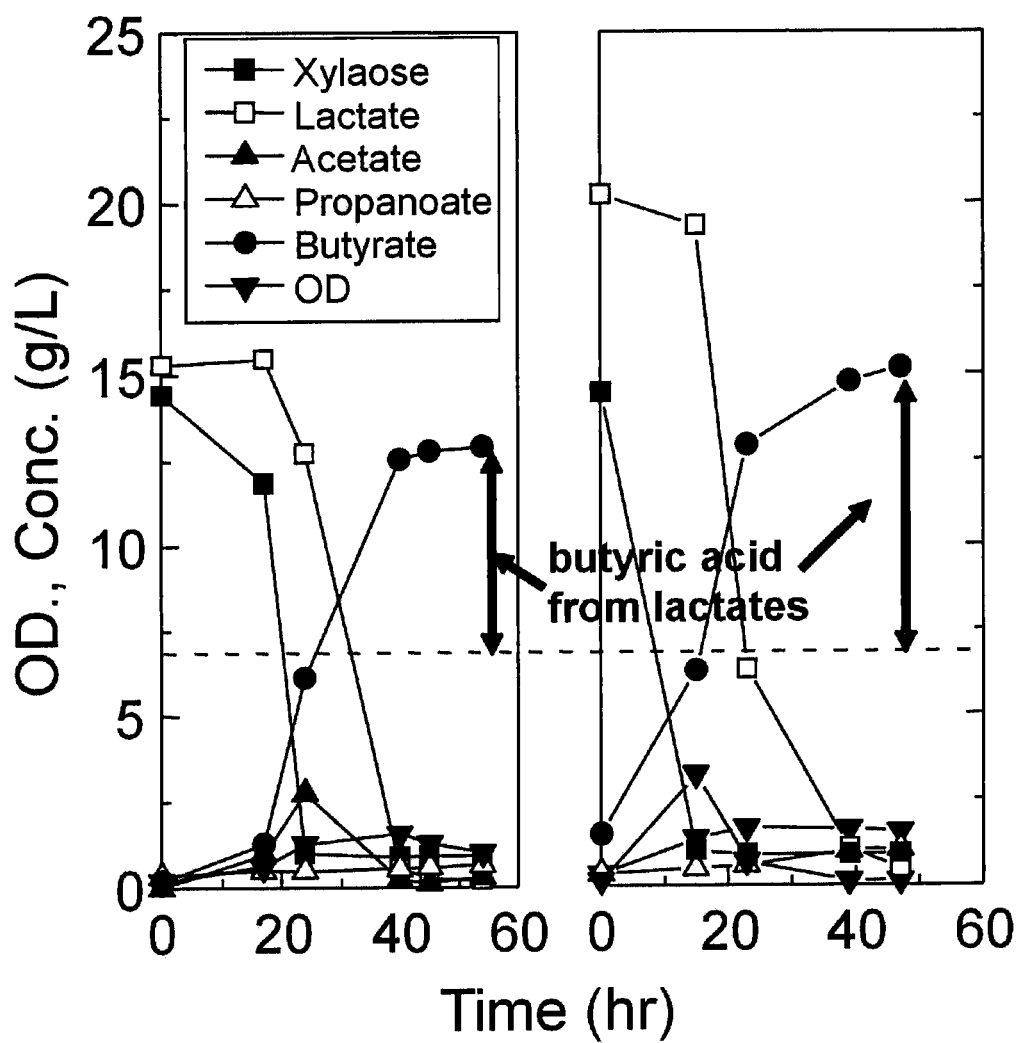

About 200 g of PVA-immobilized *C. tyrobutyricum* cell beads were packed in the packed-bed bioreactor. The fermentor was filled with 1.5 L of feedstock containing xylose and L-lactic acid. Anaerobiosis was reached by sparging the fermentor feedstock with $N_2$, and the pH of the feedstock was adjusted to 6.0 with 2 N NaOH before fermentation started. The fermentation was carried out by recirculating the medium in the fermentor through the packed-bed bioreactor at a pumping rate of 10 ml/min at 37° C. A second batch of feedstock was added to the fermentor at the 53th hour. Samples were taken at regular intervals for the analysis of free cell, substrate, and product concentrations. The time course of the substrates and product concentrations is illustrated in FIG. 13. The starting concentration of the substrates and the final carbon yields are summarized in Table 5.

TABLE 5

Carbon yield from fermentation using xylose and lactic acid as substrates

| Carbohydrate | Xylose |
|---|---|
| Carbohydrate (g/L) | 14.4 |
| L-Lactic acid (g/L) | 15.3 |
| Butyric Carbon yield | 61% |
| Total Carbon yield | 64% |
| Fermentation time | 55 hr |

The carbon yields for xylose was the average of the two feedings. Good butyric carbon yields and total carbon yields were obtained in the fermentation process using a pentose such as xylose. The experiment demonstrates that the combination of a carbohydrate other than glucose with lactic acid as substrates in fermentation exceeds those results anticipated under conventional fermentation using glucose as the only substrate, and in some instances may be deemed synergistic with the improvement of the butyric carbon yield.

Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A method of producing butyric acid, comprising:
fermenting a feedstock with at least one strain of *Clostridium* to produce butyric acid, wherein the at least one strain of *Clostridium* produces butyric acid as the predominant product in the fermentation,
wherein the feedstock comprises a substrate chosen from (i) lactic acid and (ii) lactic acid and at least one carbohydrate,
wherein when the substrate comprises lactic acid and the at least one carbohydrate, and the weight ratio of lactic acid to the at least one carbohydrate ranges from about 1 to about 10.

2. The method according to claim 1, wherein the at least one strain of *Clostridium* is chosen from *C. tyrobutyricum, C. butyricum* and *C. beijerinckii*.

3. The method according to claim 1, wherein the at least one strain of *Clostridium* is *C. tyrobutyricum*.

4. The method according to claim 1, wherein the at least one carbohydrate is chosen from monosaccharides, disaccharides, polysaccharides, and a mixture thereof.

5. The method according to claim 4, wherein the monosaccharide is chosen from glucose, xylose, galactose, and a mixture thereof.

6. The method according to claim 4, wherein the disaccharide is chosen from lactose, sucrose, cellobiose, and a mixture thereof.

7. The method according to claim 4, wherein the polysaccharide is chosen from starch, glycogen, cellulose, and a mixture thereof.

8. The method according to claim 1, further comprising treating biomass with an enzymatic saccharification process to produce the at least one carbohydrate in the feedstock.

9. The method according to claim 1, wherein the at least one strain of *Clostridium* is *C. tyrobutyricum*, and the at least one carbohydrate is glucose.

10. The method according to claim 1, wherein the method provides a butyric carbon yield greater than 66%.

11. The method according to claim 10, wherein the method provides butyric carbon yield greater than 69%.

12. The method according to claim 1, wherein the fermenting step continues for a period of time chosen from when a substantial amount of the feedstock is consumed, and when no substantial increase in butyric acid is observed.

13. The method according to claim 12, wherein the fermenting step continues for a period of time ranging from about 10 hours to about 80 hours.

14. A method of producing butyric acid, comprising:
fermenting a feedstock with at least one strain of *Clostridium* to produce butyric acid, wherein the at least one strain of *Clostridium* produces butyric acid as the predominant product in the fermentation,
wherein the feedstock comprises a substrate chosen from (i) lactic acid and (ii) lactic acid and at least one carbohydrate,
wherein when the substrate comprises lactic acid and the at least one carbohydrate, and the weight ratio of lactic acid to the at least one carbohydrate ranges from about 1 to about 10; and further wherein the lactic acid is added sequentially into the feedstock, before or after the fermenting step commences.

15. The method according to claim 14, wherein the substrate comprises lactic acid and at least one carbohydrate; and further wherein the lactic acid and the at least one carbohydrate are added sequentially into the feedstock in any order, before or after the fermenting step commences.

16. The method according to claim 14, wherein the at least one strain of *Clostridium* is chosen from *C. tyrobutyricum, C. butyricum* and *C. beijerinckii*.

17. The method according to claim 15, wherein the at least one carbohydrate is chosen from monosaccharides, disaccharides, polysaccharides, and a mixture thereof.

18. The method according to claim 15, wherein the at least one strain of *Clostridium* is *C. tyrobutyricum*, and the feedstock comprises lactic acid and glucose.

19. A method of producing butyric acid, comprising:
fermenting a feedstock with at least one strain of *Clostridium* to produce butyric acid,
wherein the feedstock comprises lactic acid and at least one carbohydrate, and the lactic acid is present in an amount greater than or equal to the amount of the at least one carbohydrate.

* * * * *